US006106820A

United States Patent [19]

Morrissey et al.

[11] Patent Number: 6,106,820
[45] Date of Patent: Aug. 22, 2000

[54] COSMETIC COMPOSITIONS

[75] Inventors: Christopher Todd Morrissey; Edward Dewey Smith, III, both of Mason; Sanjeev Midha, Blue Ash; Timothy Roy Nijakowski, Cincinnati, all of Ohio

[73] Assignee: Procter & Gamble Company, Cincinnati, Ohio

[21] Appl. No.: 09/186,541

[22] Filed: Nov. 5, 1998

Related U.S. Application Data

[63] Continuation-in-part of application No. 08/854,513, May 12, 1997.

[51] Int. Cl.$^7$ .................................................. A61K 31/74
[52] U.S. Cl. ........................................................ 424/78.18
[58] Field of Search ............................ 424/78.17, 78.18; 525/288, 301

[56] References Cited

U.S. PATENT DOCUMENTS

| | | | |
|---|---|---|---|
| 3,208,911 | 9/1965 | Oppliger | 167/87 |
| 3,862,077 | 1/1975 | Schulz | 525/285 |
| 3,862,267 | 1/1975 | Milkovich | 260/878 |
| 3,879,493 | 4/1975 | Mudde | 525/77 |
| 3,957,970 | 5/1976 | Korkis | 424/70 |
| 3,965,021 | 6/1976 | Clemens | 252/62.1 |
| 3,989,768 | 11/1976 | Milkovich | 525/285 |
| 4,030,512 | 6/1977 | Papantoniou et al. | 132/7 |
| 4,136,250 | 1/1979 | Mueller et al. | 528/29 |
| 4,185,087 | 1/1980 | Morlino | 424/70 |
| 4,277,595 | 7/1981 | Deichert et al. | 528/26 |
| 4,479,893 | 10/1984 | Hirota et al. | 252/542 |
| 4,563,347 | 1/1986 | Starch | 424/70 |
| 4,601,902 | 7/1986 | Fridd et al. | 424/70 |
| 4,636,578 | 1/1987 | Feinberg | 136/151 |
| 4,654,161 | 3/1987 | Kollmeier et al. | 252/174.15 |
| 4,659,777 | 4/1987 | Riffle et al. | 525/100 |
| 4,663,413 | 5/1987 | Ward et al. | 528/26 |
| 4,689,383 | 8/1987 | Riffle et al. | 528/12 |
| 4,693,935 | 9/1987 | Mazurek | 428/352 |
| 4,724,851 | 2/1988 | Cornwall et al. | 132/7 |
| 4,728,571 | 3/1988 | Clemens et al. | 428/352 |
| 4,733,677 | 3/1988 | Gee et al. | 132/7 |
| 4,744,978 | 5/1988 | Homan et al. | 424/70 |
| 4,814,402 | 3/1989 | Nakashima et al. | 526/245 |
| 4,902,499 | 2/1990 | Bolich, Jr. et al. | 424/70 |
| 4,963,595 | 10/1990 | Ward et al. | 525/415 |
| 4,972,037 | 11/1990 | Garbe et al. | 526/245 |
| 4,981,902 | 1/1991 | Mitra et al. | 524/547 |
| 4,981,903 | 1/1991 | Garbe et al. | 524/547 |
| 4,988,506 | 1/1991 | Mitra et al. | 424/81 |
| 5,021,477 | 6/1991 | Garbe et al. | 424/70 |
| 5,061,481 | 10/1991 | Suzuki et al. | 424/63 |
| 5,100,658 | 3/1992 | Bolich, Jr. et al. | 424/70 |
| 5,104,646 | 4/1992 | Bolich, Jr. et al. | 424/70 |
| 5,106,609 | 4/1992 | Bolich, Jr. et al. | 424/70 |
| 5,166,276 | 11/1992 | Hayama et al. | 525/329 |
| 5,219,560 | 6/1993 | Suzuki et al. | 424/63 |
| 5,229,435 | 7/1993 | Sakai et al. | 523/105 |
| 5,376,730 | 12/1994 | Niwano | 525/329.3 |
| 5,578,683 | 11/1996 | Koch | 525/301 |
| 5,622,694 | 4/1997 | Torgerson et al. | 424/70.122 |
| 5,633,317 | 5/1997 | Kawasaki | 525/66 |
| 5,730,966 | 3/1998 | Torgerson et al. | 424/70.11 |

FOREIGN PATENT DOCUMENTS

| | | | |
|---|---|---|---|
| 0 117 360 | 12/1983 | European Pat. Off. | A61K 7/06 |
| 0 408 311 A2 | 7/1990 | European Pat. Off. | C08F 230/08 |
| 0 815 848 | 1/1998 | European Pat. Off. | A61K 7/48 |
| 61-051567 | 7/1981 | Japan | A61K 07/11 |
| 56-129300 | 10/1981 | Japan | A61K 07/06 |
| 4-359912 | 6/1991 | Japan | C08F 299/08 |
| 4-359913 | 6/1991 | Japan | C08F 299/08 |
| 4-360812 | 6/1991 | Japan | A61K 7/00 |
| WO 88/05060 | 7/1988 | WIPO | C08F 30/08 |
| WO 98/48770 | 11/1998 | WIPO | A61K 7/06 |
| WO 98/48771 | 11/1998 | WIPO | A61K 7/06 |
| WO 98/48772 | 11/1998 | WIPO | A61K 7/06 |
| WO 98/48776 | 11/1998 | WIPO | A61K 7/48 |
| WO 98/49213 | 11/1998 | WIPO | C08F 290/06 |
| WO 98/51276 | 11/1998 | WIPO | A61K 7/48 |
| WO 98/51755 | 11/1998 | WIPO | C09J 151/00 |

OTHER PUBLICATIONS

U.S. application No. 08/846,058, Midha et al., filed Apr. 25, 1997.
U.S. application No. 08/842,954, Midha et al., filed Apr. 25, 1997.
U.S. application No. 08/854,513, Midha et al., filed May 12, 1997.
U.S. application No. 08/854,698, Midha et al., filed May 12, 1997.
U.S. application No. 08/858,070, Midha et al., filed May 16, 1997.
U.S. application No. 08/858,071, Midha et al., filed May 16, 1997.
U.S. application No. 08/887,450, Peffly et al., filed Jul. 2, 1997.
U.S. application No. 08/897,397, Torgerson et al., filed Jul. 21, 1997.
U.S. application No. 08/904,741, Torgerson et al., filed Aug. 1, 1997.

*Primary Examiner*—Paul R. Michl

[57] ABSTRACT

Disclosed are cosmetic compositions comprising:
  (a) from about 0.1% to about 50%, based on the weight of the composition, of a film-forming graft copolymer, wherein the copolymer comprises:
    (i) a backbone exhibiting a $T_g$ of from about 0° C. to about 50° C.; and
    (ii) one or more hydrophilic grafts attached to the backbone wherein each of the grafts exhibits a $T_g$ of from about 50° C. to about 200° C., and
  wherein the average molecular weight of each of the grafts is greater than about 1000; and
  (b) from about 50% to about 99.9%, based on the weight of the composition, of a suitable carrier.

The compositions provide good wear properties and are suitable for use in a variety of cosmetic applications, such as facial moisturizers, foundations, lipsticks, mascaras, nail polishes and the like. In a preferred embodiment, the compositions are in the form of a nail polish which, when applied to nails, exhibit excellent long wear properties.

3 Claims, No Drawings

COSMETIC COMPOSITIONS

This application is a CIP of Ser. No. 08/854,513, filed May 12, 1997.

TECHNICAL FIELD

The present invention relates to compositions useful as cosmetic or therapeutic agents. The compositions are particularly useful as nail polishes, and are especially useful as topcoat compositions.

BACKGROUND OF THE INVENTION

"Cosmetic compositions" as used herein refer to products generally recognized as being formulated for beautifying or grooming the skin (especially the face), lips, eyes or nails. For example, cosmetic compositions such as lotions, creams, emulsions, packs, make-up (e.g., foundations, lipsticks, nail polish, eye shadows and the like) are used to improve one's outward appearance. For many of these applications, it is desirable that the composition provide long wear.

In particular, consumers use nail polishes to cosmetically enhance their nails or protect the nails from everyday conditions and stressors. However, these nail polish compositions are deficient in many respects, including their inability to provide long wear. Nail polishes which are known or currently available often exhibit deterioration, particularly in the form of chipping or peeling, in as few as one or two days. Such poor wear often forces consumers to remove their nail polish soon after original application and reapply additional nail polish to the nails. Consumers may also attempt to correct the unsightly appearance of the deteriorating nail polish by "touching-up" the areas of the nail which exhibit the deterioration, a practice which actually impairs the overall look of the nail polish. Finally, consumers may choose to do nothing about the deterioration and allow, for example, chipping and peeling to progress, resulting in nails which are not only minimally protected from the environment but are unsightly as well.

The art is replete with nail polish compositions which are promoted as having long wear, and/or resistance to chipping. While some nail polish compositions provide better wear than others, a need remains for nail polish compositions having improved wear properties.

The present inventors have surprisingly discovered that the present compositions provide excellent long wear properties including, for example in the case of nail polishes, chip-resistance and superior hardness. These compositions have preferred toughness properties for deflecting environmental stressors which contribute to wear. The compositions exhibit long wear at a superior level not provided by the nail polishes which are presently known and used.

SUMMARY OF THE INVENTION

The present invention relates to cosmetic compositions having improved wear, preferably comprising:
(a) from about 0.1% to about 50%, based on the weight of the composition, of a film-forming graft copolymer, wherein the copolymer comprises:
  (i) a backbone exhibiting a $T_g$ of from about 0° C. to about 50° C.; and
  (ii) one or more hydrophilic grafts attached to the backbone wherein each of the grafts exhibits a $T_g$ of from about 50° C. to about 200° C., and
wherein the average molecular weight of each of the grafts is greater than about 1000; and (b) from about 50% to about 99.9%, based on the weight of the composition, of a suitable carrier.

In a preferred embodiment, the carrier comprises from about 10% to about 98%, based on the weight of the composition, of a volatile organic diluent.

The present compositions are suitable for use in a variety of cosmetic applications, such as facial moisturizers or other treatments, foundations, lipsticks, mascaras, nail polishes and the like, and provide improved wear. In a preferred embodiment, the compositions are in the form of a nail polish which, when applied to nails, exhibit excellent long wear properties.

The present invention also relates to films formed from the compositions, kits comprising the compositions, and methods of treating the skin, lips, nails or eyelashes comprising application of the composition to the substrate.

DETAILED DESCRIPTION OF THE INVENTION

The essential components of the present invention are described herein below. Also included are non-limiting descriptions of various optional and preferred components useful in the compositions of the present invention.

The present invention can comprise, consist of, or consist essentially of any of the required or optional components and/or limitations described herein.

All percentages and ratios are calculated by weight unless otherwise indicated. All percentages are calculated based on the total composition unless otherwise indicated.

All component or composition levels are in reference to the active level of that component or composition, and are exclusive of impurities, for example, residual solvents or by-products, which may be present in commercially available sources.

Referred to herein are trade names for materials including, but not limited to, polymers and optional components. The inventors herein do not intend to be limited by materials under a certain trade name. Equivalent materials (e.g., those obtained from a different source under a different name or catalog (reference) number) to those referenced by trade name may be substituted and utilized in the compositions, films, kits and methods herein.

All documents referred to herein, including all patents, patent applications, and printed publications, are hereby incorporated by reference in their entirety.

The compositions of the present invention are suitable for topical application. As used herein, the term "suitable for topical application" means that the compositions are suitable for use in contact with skin, lips, nails, and/or eyelids without undue toxicity, incompatibility, instability, allergic response, and the like. In a preferred embodiment, the compositions are nail polishes which are accordingly suitable for use in contact with the nails. The term "nail polish," as well known in the art describes a composition which is to be applied to the nails and which forms a durable film and provides benefits to the nail, such as aesthetic (e.g., color, shine), therapeutic, or prophylactic benefits. As used herein, a nail polish may consist of the compositions described herein, as well as systems/kits comprising such compositions.

In addition to human applications, the present compositions may be formulated for analogous topical application to other mammals or non-mammals.

Compositions of the Present Invention

The present inventors have discovered compositions which, when applied topically, provide films exhibiting improved wear. In particular, the compositions, when applied to nails, provide films exhibiting excellent long wear. Without intending to be limited by theory, it is believed that the compositions of the present invention are beneficial to long wear because they provide films which deflect environmental stressors by virtue of their hardness, toughness, durability, rigidity, and/or resistance to chipping.

I. Film-Forming Graft Copolymer

The present compositions comprise a film-forming graft copolymer. The graft copolymer tends to contribute to the wear benefits of the present invention. For example, the beauty benefits provided by a composition tend to last longer, and/or the composition as applied tends to last longer, relative to a composition not containing the graft copolymer of the present invention.

As used herein, the term "film-forming" means that the copolymer to which it refers forms an adherent continuum from a composition when applied to a substrate. See, e.g., *Polymer Colloids,* Robert M. Fitch, ed., New York: Plenum Press, pp. 173–183 (1971). The term "graft" in reference to a polymer, especially herein a copolymer, is familiar to one of ordinary skill in the art. As used herein, the term "graft" describes copolymers that have "grafted" polymeric side chain moieties ("grafts") covalently bonded to another portion of the polymer which is referred to as the "backbone". Thus, graft copolymers can be described as polymers having pendant polymeric side chains, and as being formed from the "grafting" or covalent bonding of polymeric side chains onto a backbone.

The compositions of the present invention preferably comprise at least about 0.1%, by weight of the composition, of the film forming graft copolymer. More preferred compositions comprise from about 1% to about 50%, preferably from about 2% to about 40%, more preferably from about 5% to about 30%, and most preferably from about 10% to about 25%, by weight of the composition, of the film-forming graft copolymer.

The graft copolymers of the present invention have a weight average molecular weight of at least about 20,000. There is no upper limit for molecular weight except that which limits applicability of the invention for practical reasons such as, for example, processing, aesthetic characteristics, and ease of formulation. Generally, the weight average molecular weight is less than about 10,000,000, more generally less than about 5,000,000, and typically less than about 3,000,000. Preferably, the weight average molecular weight is from about 50,000 to about 2,000,000, more preferably from about 75,000 to about 1,000,000, and most preferably from about 80,000 to about 750,000.

The graft copolymers of the present invention exhibit one or more glass transition temperatures ($T_g$). Preferred copolymers have at least two distinct immiscible phases, wherein the essential, hydrophilic polymeric side chains are closely associated with each other and exist in one phase and the polymeric backbone of the copolymer remains in a second separate phase. As a consequence of this phase immiscibility, the copolymer may exhibit at least two distinct Tg values, namely one $T_g$ value for the backbone and one $T_g$ value for the side chains, if the temperature separation between each of the $T_g$ values involved is large enough.

Where the graft copolymer optionally comprises one or more other side chains, e.g., polysiloxane side chains according to one embodiment of the invention, the copolymer may also exhibit one or more third $T_g$'s corresponding to the other side chains. Whether such additional $T_g$ values are observable depends upon a number of factors including, but not limited to, the number of side chains on the graft copolymer, the temperature separation between each of the $T_g$ values involved, and in the case of polysiloxane side chains, the percent silicone in the graft copolymer.

The essential backbone and side chains of the graft copolymer are derived from monomers. The side chains comprise at least one type of hydrophilic monomer, and optionally one or more types of hydrophobic monomers. The backbone may be derived from hydrophilic monomers, hydrophobic monomers, or mixtures thereof. Suitable monomers are selected such that the overall copolymer is soluble or dispersible in the carrier of choice. The selection of suitable monomers for a given carrier of choice can be readily made by those skilled in the art. In general, one skilled in the art chooses monomers which form homopolymers that are soluble or dispersible in the carrier of choice, and uses a majority of those in the graft copolymer.

As used herein, "soluble" means that the material so described (e.g., the copolymer) is soluble in a designated carrier (e.g., the carrier of choice) at 25° C. at a concentration of at least about 20 mg/mL, more preferably at least about 50 mg/mL, and most preferably at least about 100 mg/mL. By "dispersible" is meant that the material so described forms a stable, uniform suspension (without the addition of further materials such as emulsifiers; includes latexes and pseudolatexes) when combined with the designated carrier at 25° C. at a concentration of at least about 20 mg/mL, more preferably at least about 50 mg/mL, and most preferably at least about 100 mg/mL.

As used herein, "hydrophilic" means that the material so described is soluble or dispersible in water, lower alcohols ($C_1$–$C_4$), or mixtures of water and lower alcohols. As used herein, "hydrophobic" means that the material so described is not soluble or dispersible in water, lower alcohols ($C_1$–$C_4$), or mixtures of water and lower alcohols. As used herein in reference to a monomer, hydrophilic or hydrophobic refers to the property of a homopolymer of the monomer.

The graft copolymers can be nonionic, ionic (anionic or cationic), amphoteric, or zwitterionic.

Graft polymers suitable for use herein include those described in commonly assigned, copending U.S. patent application Ser. No. 08/854,513 (Attorney's Docket 6629); Ser. No. 08/854,698 (Attorney's Docket 6630); both filed May 12, 1997; and Ser. No. 08/858,070 (Attorney's Docket 6637) and Ser. No. 08/858,071 (Attorney's Docket 6638); both filed May 16, 1997; all filed in the names of Midha and Nijakowski; and incorporated herein by reference in their entirety.

a) Backbone of the Graft Copolymer

The backbones of the graft copolymers comprise from about 50% to about 98%, preferably from about 60% to about 95%, and more preferably from about 70% to about 90%, by weight of the backbone, of vinyl monomer units. The backbone exhibits a $T_g$ of from about 0° C. to about 50° C., preferably from about 0° C. to about 45° C., more preferably from about 0° C. to about 35° C., and most preferably from about 0° C. to about 25° C.

The backbone vinyl monomer units are derived from copolymerizable monomers (including macromonomers such as described herein, infra), preferably ethylenically unsaturated monomers. As used herein, the term "copolymerizable" means that the monomer may be reacted with or polymerized with other monomers or macromonomers in a polymerization reaction using one or more conventional synthetic techniques, such as ionic, emulsion, dispersion, Ziegler-Natta, free radical, group transfer or step growth polymerization. The term "ethylenically unsaturated" is used herein to mean a material that contains at least one polymerizable carbon—carbon double bond, which can be mono-, di-, tri- or tetra-substituted.

Preferred monomers include unsaturated alcohols, unsaturated monocarboxylic acids, unsaturated dicarboxylic acids, unsaturated anhydrides, alcohol esters of unsaturated monocarboxylic acids, alcohol esters of unsaturated dicarboxylic acids, alcohol esters of unsaturated anhydrides, alkoxylated esters of unsaturated monocarboxylic acids, alkoxylated esters of unsaturated dicarboxylic acids, alkoxylated esters of unsaturated anhydrides, aminoalkyl esters of unsaturated monocarboxylic acids, aminoalkyl esters of unsaturated dicarboxylic acids, aminoalkyl esters of unsaturated anhydrides, amides of unsaturated monocarboxylic acids, amides of unsaturated dicarboxylic acids, amides of unsaturated anhydrides, salts of unsaturated monocarboxylic acids, salts of unsaturated dicarboxylic acids, salts of unsaturated anhydrides, unsaturated hydrocarbons, unsaturated heterocycles, and mixtures thereof. These monomers typically comprise 2 to 30 carbon atoms.

More preferred monomers are selected from the group consisting of acrylic acid, methacrylic acid, N,N-dimethylacrylamide, N,N-dialkylaminoalkyl(meth)acrylate, N,N-dialkylaminoalkyl(meth)acrylamide, N,N-dimethylaminoethyl methacrylate, quaternized dimethylaminoethyl methacrylate, vinyl pyrrolidone, $C_1$–$C_{18}$ alkyl esters of acrylic or methacrylic acid, styrene, a-methylstyrene, t-butylstyrene, 4-hydroxystyrene, 4-acetoxystryrene, vinyl acetate, vinyl propionate, vinyl chloride, vinylidene chloride, vinyl toluene, 2-methoxyethyl acrylate, n-butyl methacrylate, iso-butyl methacrylate, t-butyl acrylate, t-butyl methacrylate, 2-ethylhexyl methacrylate, methyl methacrylate, and salts and mixtures thereof.

Typical counterions for the salts of anionic monomers include inorganic, (alkali, alkaline earth metals, or transition metals) or organic (ammonium or alkylammonium including mono, di, tri and tetraalkyl) cations and the like, provided that the overall solubility or dispersibility of the polymer in the carrier is not adversely affected. Typical counterions for the salts of cationic monomers include halides, sulfates, sulfonates, phosphates, nitrates, and the like, provided that the overall solubility or dispersibility of the polymer in the carrier is not adversely affected.

The most preferred monomers are selected from the group consisting of acrylic acid, methacrylic acid, 2-methoxyethyl acrylate, N,N-dimethylaminoethyl methacrylate, n-butyl methacrylate, iso-butyl methacrylate, t-butyl acrylate, t-butyl methacrylate, 2-ethylhexyl methacrylate, methyl methacrylate, and mixtures thereof.

b) Hydrophilic Grafts (Side Chains) of the Graft Copolymer

The copolymers of the present invention comprise from about 2% to about 50%, preferably from about 5% to about 40%, and more preferably from about 10% to about 30%, by weight of the graft copolymer, of hydrophilic side chains. Typically, the weight average molecular weight of the side chains is from about 1000 to about 50,000. The hydrophilic side chains exhibit a $T_g$ of from about 50° C. to about 200° C., preferably from about 60° C. to about 150° C., and most preferably from about 70° C. to about 110° C.

A preferred method for copolymer preparation utilizes one or more types of macromonomers to provide the side chain grafts. The macromonomers that are useful herein contain a polymeric portion and a moiety which is copolymerizable with the vinyl monomers comprising the backbone. That is, the macromonomers can be reacted with or polymerized with the vinyl monomers of the backbone in a polymerization reaction using one or more conventional synthetic techniques such as described herein. The copolymerizable moiety is preferably an ethylenically unsaturated moiety. Preferred macromonomers are endcapped with a vinyl moiety which is copolymerizable with the backbone monomer units. As used herein, the term "endcapped" means that the vinyl moiety is at or near a terminal position of the macromonomer.

The macromonomers may be synthesized utilizing a variety of standard synthetic procedures known to one of ordinary skill in the art. Furthermore, these macromonomers may be synthesized starting from commercially-available starting materials.

Preferred macromonomers are polyacrylate, polymethacrylate, polyoxazolines, polypyridines, or copolymers thereof.

Suitable macromonomers include those exemplified by the general formula:

wherein I is an optionally present initiator, n is an integer from 0 to 1, W is a monomer unit, m is an integer of from about 10 to about 2000, and E is an endcapping group.

Without being limited by theory, I can be derived from a chemical initiator or solvent used in the synthesis of the macromonomer. Nonlimiting examples of initiators from which I may be derived include hydrogen ion, hydrogen radical, hydride ion, hydroxide ion, hydroxyl radical, peroxide radical, peroxide anion, $C_1$–$C_{20}$ carbocations, $C_1$–$C_{20}$ carbanions, $C_1$–$C_{20}$ carbon radicals, $C_1$–$C_{20}$ aliphatic and aromatic alkoxy anions, ammonium ion, and substituted ammonium ions (e.g., $C_1$–$C_{20}$ alkyl and $C_1$–$C_{20}$ alkoxy substituted), and mixtures thereof. I may also be derived from any useful solvent including, for example, water, methanol, ethanol, propanol, iso-propanol, acetone, hexane, dichloromethane, chloroform, benzene, toluene, and mixtures thereof.

W is derived from monomers selected from the group consisting of hydrophilic monomers, and mixtures of hydrophilic monomers with hydrophobic monomers, provided that the overall macromonomer is hydrophilic.

Preferred is when W is a monomer selected from the group consisting of oxazolines, N-alkyloxazolines, alkylene glycols, N-vinylpyrrolidones, N-allylpyrrolidones, vinylpyridines, allylpyridines, vinylcaprolactams, allylcaprolactams, vinylimidazoles, allylimidaoles, vinylfurans, allylfurans, vinyltetrahydrofurans, allyltetrahydrofurans, vinylaminobenzenes, vinylaminomethylbenzenes, vinylaminoethylbenzenes, N,N-dialkylacrylamides, N,N-dialkyl(alkyl)acrylamides, acrylic acid, methacrylic acid, phenyl methacrylate, benzyl methacrylate, and $C_1$–$C_{18}$ alkyl esters of acrylic or methacrylic acid, styrene, a-methylstyrene, t-butylstyrene and mixtures thereof. More preferable monomers include acrylic acid, methacrylic acid, n-propyl methacrylate, iso-butyl methacrylate, t-butyl acrylate, t-butyl methacrylate, 2-hydroxyethyl methacrylate, 2-hydroxypropyl methacrylate, iso-propyl methacrylate, methylmethacrylate, styrene, oxazoline, 2-ethyl-2-oxazoline, 2-methyl-2-oxazoline, vinylpyridine, and mixtures thereof. The most preferable monomers include acrylic acid, methacrylic acid, n-propyl methacrylate, iso-butyl methacrylate, iso-propyl methacrylate, methylmethacrylate, 2-ethyl-2-oxazoline, vinylpyridines, and mixtures thereof.

c) Optional Components of the Graft Copolymer

The graft copolymers may further comprise one or more polysiloxane macromonomers, preferably exemplified by the general formula:

$$X\text{-}Y_n\text{-}Si\text{-}R_{3-m}\text{-}Z_m$$

wherein X is a vinyl group copolymerizable with the backbone vinyl monomers, Y is a divalent linking group, each R is independently selected from hydrogen, hydroxyl, $C_1$–$C_6$ alkyl, $C_1$–$C_6$ alkoxy, $C_2$–$C_6$ alkylamino, phenyl, $C_1$–$C_6$ alkyl, and alkoxy-substituted phenyl, Z is a polysiloxane moiety having an average molecular weight of at least about 1000 and is essentially unreactive under copolymerization conditions, n is an integer from 0 to 1, and m is an integer from 1 to 3.

The polysiloxane macromonomer has an average molecular weight from about 1000 to about 50,000, preferably from about 5,000 to about 30,000, and more preferably from about 8,000 to about 25,000.

Preferably, the polysiloxane macromonomer has a structure selected from one of the following three structures:

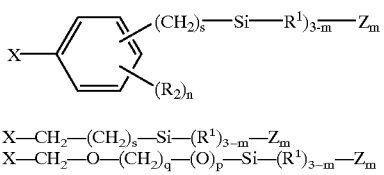

X—CH$_2$—(CH$_2$)$_s$—Si—(R$^1$)$_{3-m}$—Z$_m$
X—CH$_2$—O—(CH$_2$)$_q$—(O)$_p$—Si—(R$^1$)$_{3-m}$—Z$_m$ wherein s is an integer from 0 to 6, preferably 0, 1, or 2, more preferably 0 or 1, m is an integer from 1 to 3, preferably 1, p is an integer from 0 to 1, q is an integer from 2 to 6, each $R^1$ is independently selected from hydrogen, hydroxyl, $C_1$–$C_6$ alkyl, $C_1$–$C_6$ alkoxy, $C_1$–$C_6$ alkylamino, phenyl, $C_1$–$C_6$ alkyl phenyl, and $C_1$–$C_6$ alkoxy-substituted phenyl, preferably $C_1$–$C_6$ alkyl, $C_1$–$C_6$ alkyl phenyl, and $C_1$–$C_6$ alkoxy-substituted phenyl, more preferably $C_1$–$C_6$ alkyl, even more preferably methyl, $R^2$ is selected from $C_1$–$C_6$ alkyl and $C_1$–$C_6$ alkyl substituted phenyl, preferably methyl, n is an integer from 0 to 4, preferably 0 to 1, more preferably 0, X is:

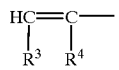

wherein $R^3$ is selected from hydrogen and —COOH, preferably hydrogen, $R^4$ is selected from hydrogen, methyl, and —CH$_2$COOH, preferably methyl, Z is:

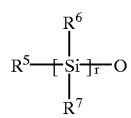

wherein $R^5$, $R^6$, and $R^7$, are, independently, selected from hydrogen, hydroxyl, $C_1$–$C_6$ alkyl $C_1$–$C_6$ alkoxy, $C_2$–$C_6$ alkylamino, phenyl, $C_1$–$C_6$ alkyl, $C_1$–$C_6$ alkoxy-substituted phenyl, hydrogen, and hydroxyl, preferably $C_1$–$C_6$ alkyl, more preferably methyl, and r is an integer from about 14 to about 700, preferably about 60 to about 400, and more preferably about 100 to about 350.

d) Exemplary Graft Copolymers

Nonlimiting examples of graft copolymers for use in the present invention are:

1. Poly(t-butyl acrylate-co-2-methoxyethyl acrylate-co-methacrylic acid)-graft-poly (n-propyl methacrylate-co-methacrylic acid); average molecular weight ($M_w$) 149,900; backbone, 80% of $M_w$ of graft copolymer; backbone composition: t-butyl acrylate (53%), 2-methoxyethyl acrylate (36%), methacrylic acid (11%); macromonomer: 20% of $M_w$ of graft copolymer; macromonomer composition: n-propyl methacrylate (65%); methacrylic acid (35%); macromonomer $M_w$ 6,000.

2. Poly(t-butyl acrylate-co-2-methoxyethyl acrylate-co-methacrylic acid)-graft-poly (iso-butyl methacrylate-co-methacrylic acid); $M_w$ 55,000; backbone, 80% of $M_w$ of graft copolymer; backbone composition: t-butyl acrylate (53%), 2-methoxyethyl acrylate (36%), methacrylic acid (11%); macromonomer: 20% of $M_w$ of graft copolymer; macromonomer composition: iso-butyl methacrylate (65%); methacrylic acid (35%); macromonomer $M_w$ 8,000.

3. Poly(t-butyl acrylate-co-2-methoxyethyl acrylate-co-acrylic acid)-graft-[poly (n-propyl methacrylate-co-methacrylic acid) poly(dimethylsiloxane)]; $M_w$ 83,000; backbone, 77% of $M_w$ of graft copolymer; backbone composition: t-butyl acrylate (43%), 2-methoxyethyl acrylate (38%), acrylic acid (18%); macromonomers: 17% of $M_w$ of graft copolymer; macromonomer composition: n-propyl methacrylate (60%); methacrylic acid (40%); macromonomer $M_w$ 6,000; poly(dimethylsiloxane) macromonomers: 6% of $M_w$ of graft copolymer; poly(dimethylsiloxane): $M_w$ 10,000.

4. Poly(t-butyl acrylate-co-2-methoxyethyl acrylate-co-acrylic acid)-graft-[poly (n-propyl methacrylate-co-methacrylic acid) poly(dimethylsiloxane)]; $M_w$ 250.000; backbone, 74% of $M_w$ of graft copolymer; backbone composition: t-butyl acrylate (31%), 2-methoxyethyl acrylate (44%), acrylic acid (24%); macromonomers: 20% of $M_w$ of graft copolymer; macromonomer composition: n-propyl methacrylate (78%); methacrylic acid (220%); macromonomer $M_w$ 12,000; poly(dimethylsiloxane) macromonomers: 6% of $M_w$ of graft copolymer; $M_w$ 10,000.

5. Poly(t-butyl acrylate-co-2-methoxyethyl acrylate)-graft-[poly (2-ethyl 2-oxazoline) poly(dimethylsiloxane)]; average molecular weight $M_w$ 150,000, backbone, 85% of $M_w$ of graft copolymer; backbone composition t-butyl acrylate(82%), 2-methoxyethyl acrylate(1 8%), macromonomers: 12% of $M_w$ of graft copolymer; poly (2-ethyl-2-oxazoline) macromonomer $M_w$ 2,500; poly (dimethylsiloxane) macromonomer 3% of $M_w$ of graft copolymer; $M_w$ 10,000.

6. Poly((t-butyl acrylate-co-2-methoxyethyl acrylate-co-methacrylic acid)-graft-poly (2-ethyl 2-oxazoline)); average molecular weight ($M_w$) 110,000; backbone, 80% of $M_w$ of graft copolymer; backbone composition: 1-butyl acrylate (53%), 2-methoxyethyl acrylate (36%), methacrylic acid (11%); macromonomers: 20% of $M_w$ of graft copolymer; 2-ethyl-2-oxazoline macromonomer $M_w$ 4500.

7. Poly((iso-butyl methacrylate-co-2-ethylhexyl methacrylate)-graft-poly (2-ethyl 2-oxazoline)); average molecular weight ($M_w$) 50,000; backbone, 95% of $M_w$ of graft copolymer; backbone composition: iso-butyl methacrylate (44%), 2 ethylhexyl methacrylate (56%); macromonomer: 5% of $M_w$ of graft copolymer; 2-ethyl-2-oxazoline macromonomer, $M_w$ 2,500.

e) Synthesis of the Graft Copolymer

The graft copolymers may be synthesized by a variety of techniques known to one skilled in the art. These include attaching preformed grafts to preformed backbones ("grafting onto"), polymerizing grafts from preformed backbones ("grafting from"), and copolymerizing monomers with macromonomers. The backbones and grafts can be polymerized by a variety of techniques including radical, cationic, anionic. Ziegler-Natta, group transfer polymerization, step growth polymerization, or combinations thereof. The polymerizations can optionally be "living" or "living-like" polymerizations such as are known to those skilled in the art. Preferably, the copolymers are synthesized by free radical polymerization of the backbone monomers with side chain macromonomers, or the polymerization of grafts from existing backbones ("grafting from"). The general principles of free radical polymerization methods are well known to one skilled in the art. See e.g., Odian, "Principles of Polymerization", 3rd ed., John Wiley & Sons, pp. 198–334 (1991).

For example, the desired vinyl monomers and macromonomers are placed in a reactor, along with a sufficient amount of a solvent so that when the reaction is complete the viscosity of the reaction is reasonable. Undesired terminators, especially oxygen, are removed as needed, for example, by evacuation or by purging with an inert gas. The initiator is introduced and the reaction is brought to the temperature needed for initiation to occur, wherein thermal initiators are used. Alternatively, redox or radiation initiation may be used. The polymerization is allowed to proceed as long as needed for a high level of conversion to be achieved, typically from a few hours to a few days. The solvent is removed, typically by evaporation or by precipitating the copolymer. The copolymer may be further purified, as desired.

As an alternative to a batch reaction, the copolymer may be made by a semi-continuous or continuous process. In the semi-continuous process, two or more additions of monomers or macromonomers are made during the polymerization reaction. This is advantageous wherein the copolymer is made of several monomers which react during the polymerization at different rates. The proportions of monomers added to the reaction at the separate points of addition may be adjusted by one of ordinary skill in the art such that the polymers of the final product have a more uniform structure. In other words, the polymers of the final product will have a more consistent monomer content distribution for each of the monomer types charged to the reaction.

The copolymers according to the above method are prepared by the polymerization combination of vinyl monomers and macromonomers. The copolymer composition is characterized by the amount of each monomer charged to the polymerization reaction vessel, or alternatively, used in a continuous or semi-continuous process.

In an alternative method, the grafts are polymerized from existing backbones. A particularly preferred synthetic method involves two essential reaction steps. In the first reaction step, the polymeric backbone of the graft polymer is first prepared. This is accomplished by reacting copolymerizable monomers to form a polymeric backbone containing a plurality of organic halide moieties covalently bonded to and pendant from the polymeric backbone, and includes those polymers which conform generally to the formula

[A]$_a$[B]$_b$
|
C

where "A" is a monomer unit having an organic halide moiety "C" attached which is covalently bonded to and pendant from the "A" monomer unit, and "B" is a monomer unit that is copolymerizable with the "A" monomer unit, "a" is a positive integer having a value of 2 or greater, preferably a value of from about 2 to about 30, and "b" is a positive integer having a value of at least about 4, preferably a value of from about 10 to about 2000. The organic halide moiety "C" includes any linear, branched or cyclic (aromatic or otherwise) carbon structure, whether substituted or unsubstituted, which also contain a halogen atom (Cl, Br or I).

In the first reaction step of this synthesis, the "A" monomer unit with the attached organic halide moiety "C" is preferably selected from the group of allyl monomers, vinyl acetate monomers, acid halide monomers, styryl monomers, or combination thereof, and more preferably selected from the monomer units characterized by the following general structures (Groups I–V):

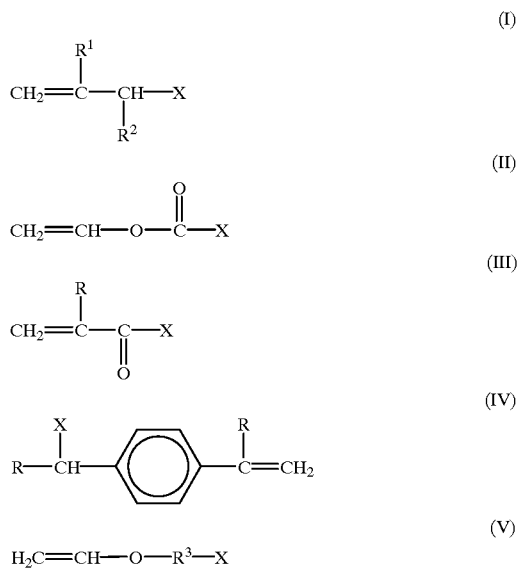

where R is methyl or hydrogen; X is a halogen atom (Cl, Br, I); $R^1$ and $R^2$ are each independently selected from methyl, hydrogen or methoxy; and $R^3$ is an alkyl group having from 1 to 8 carbon atoms.

The first reaction step involves any conventional or otherwise known polymerization techniques such as ionic, Ziegler-Natta, free radical, group transfer or step growth polymerization, or combinations thereof. The first reaction step preferably involves conventional free radical polymerization techniques. Once the first reaction is complete, or has progressed to the extent desired, the first reaction step is terminated or allowed to terminate depending on the polymerization method selected, the degree or extent of polymerization desired, the reactivity of the monomer units selected for use in the reaction, and so forth. Any conventional or otherwise known termination technique appropriate for the selected reaction and reaction conditions may be used. For example, and most typically, after polymerization of the polymeric backbone by free radical polymerization, the reaction mixture is heated to about 120° C. for about 15 minutes to consume or react any remaining free radical initiator, and thereafter the reaction mixture is cooled or allowed to cool to room temperature to allow the reaction to self terminate before addition of ingredients to start the second reaction step.

In the second reaction step, the polymeric backbone described hereinabove is reacted with one or more copolymerizable monomers in the presence of a catalytic amount of a transition metal salt, preferably a Cu(I) salt and preferably complexed to a suitable ligand. In this reaction step, the organic halide moieties act as initiators in the presence of the copolymerizable monomers and the catalyst, resulting in the grafting of the monomers onto the polymeric backbone by atom transfer free radical polymerization, the monomers forming a plurality of polymeric side chains covalently bonded to and pendant from the backbone. The polymeric side chains form on the polymeric backbone without the need to use copolymerizable macromonomers to achieve the pendant polymeric graft chains.

Suitable monomers in the second reaction step include those described herein above in regard to the macromonomer.

The catalyst for the second reaction step is a transition metal salt, preferably a Cu(I) salt such as Cu(I) halide salts (Cl, F, Br, I) and which is preferably complexed to a ligand which is suitable for solubilizing the Cu(I) salt in the reaction mixture, wherein the reaction mixture of the second reaction step comprises dissolved or partially dissolved polymer, unreacted monomer, solvent and catalyst. Preferred ligands for use in solubilizing the Cu(I) salts in the reaction mixture are aprotic bidendates such as diphosphates, 2,2' bipyridyl, C1–C20 alkyl substituted bipyridyl (4,4'-di-5-nonyl-2,2'-bipyridine, 4,4'-di-t-butylbipyridine, 4,4'-diheptyl-2,2'-bipyridine) and combinations thereof. Most preferred is 2,2' bipyridyl complexed to a Cu(I) halide salt, especially Cu(I) Cl. Other conventional or otherwise known ligands can be used herein provided that they do not substantially and unduly impair the polymerization reaction of the process herein, some examples of which are described in "The Use of Living Radical Polymerization to Synthesize Graft Copolymers" Dept. of Chemistry, Carnegie Mellon University, Pittsburgh, Pa.; Simion Cocoa and Krzysztof Matyjaszewski, Polymer Preprints, Vol. 37(1), pg. 571–572, 1996. "Alternating Copolymers of Methyl Acrylate with Isobutene and Isobutyl Vinyl Ether using ATRP" Dept. of Chemistry, Carnegie Mellon University, Pittsburgh, Pa.; Timothy e. Patten et al.Polymer Preprints, Vol. 37(1), pg. 573–574, 1996., "Radical Polymerization yielding Polymers with Mw/Mn ~1.05 by Homogeneous Atom Transfer Radical Polymerization" Carnegie Mellon University, Pittsburgh, Pa.; T. F. Patten et al.Polymer Preprints, Vol. 37(1), pg. 575–576, 1996. "The Synthesis of End Functional Polymers by Living Radical Polymerization" Carnegie Mellon University, Pittsburgh, Pa., Y. Nakagawa et al., Polymer Preprints, Vol. 37(1), pg. 577–578, 1996, which publications are incorporated herein by reference.

The copolymers of the present invention can be used alone or with low levels of the corresponding copolymers having no side chains grafted to the backbone. As is known in the art, synthetic graft copolymerization processes may produce a mixture of polymer molecules containing none, one, or more than one side chains covalently bonded to and pendant from the polymeric backbone. From knowledge of the amount and average molecular weight of side chains in a polymer sample, and the average molecular weight of the polymer sample, it is possible to calculate the average number of side chains per polymer backbone.

II) Carriers of the Present Invention

The compositions of the present invention comprise a carrier, or vehicle, which is suitable for topical application, as a support for the graft copolymer. Such carriers are well-known to one of ordinary skill in the art, and include one or more compatible liquid diluents or vehicles which are suitable for topical application. The carrier may optionally also contain one or more compatible solid filler diluents or vehicles which are suitable for topical application. The carrier may comprise one or more active or inactive materials, including but not limited to optional components described below. The graft copolymers herein are soluble or dispersible in (dissolved or dispersed in) at least one liquid diluent. In single phase systems, the copolymer is soluble or dispersible in the liquid diluent component mixture. In multiple phase systems, e.g., emulsions, the copolymer is soluble or dispersible in at least one liquid diluent.

The compositions of the present invention generally comprise from about 50% to about 99.9% of the carrier by weight of the composition. The amount of carrier varies depending on the cosmetic application desired. The compositions preferably comprise from about 60% to about 98%, more preferably from about 70% to about 95%, also preferably from about 75% to about 90%, carrier by weight of the composition. For example, preferred compositions comprise 74% to about 99.7%, more preferably from about 79% to about 99%, carrier by weight of the composition.

Suitable liquid diluents may be hydrophilic, hydrophobic, or a combination thereof. The diluents may be organic, inorganic, or a mixture thereof. The liquid diluent may be volatile, non-volatile, or a mixture thereof. Preferred liquid diluents comprise a volatile diluent. By "volatile" it is meant that the diluent exhibits a significant vapor pressure at ambient conditions (e.g., 1 atmosphere, 25° C.), as is understood by those in the art, and has a boiling point at one atmosphere of 260° C. or less. Preferred volatile organic diluents have a boiling point of from about 50° C. to about 140° C., and more preferably from about 56° C. to about 125° C., at atmospheric pressure.

Volatile diluents include water, alcohols, esters, ketones, ethers, aromatic hydrocarbons, aliphatic hydrocarbons and siloxanes. Preferred alcohols, esters, ketones, and ethers are $C_1$ to about $C_{10}$, more preferably $C_1$ to $C_4$. Preferred aromatic hydrocarbons and aliphatic hydrocarbons are $C_6$ to about $C_{18}$. For nail polish compositions of the present invention, preferred organic diluents are selected from $C_1$ to about $C_{10}$ (preferably $C_1$ to $C_4$) alcohols, esters, ketones, and mixtures thereof; more preferably such alcohols, esters and mixtures thereof.

Preferred alcohols are monohydric. The most preferred monohydric alcohols are selected from ethanol, isopropanol, n-propanol, and butanol. The most preferred esters are selected from ethyl acetate and butyl acetate.

Preferred aliphatic hydrocarbons are branched chain hydrocarbons, preferably characterized by a boiling point of at least about 105° C., more preferably at least about 110° C., even more preferably at least about 125° C., most preferably at least about 150° C. The boiling point is also generally about 260° C. or less, preferably about 200° C. or less. The branched chain hydrocarbon diluents are preferably selected from the group consisting of $C_{10}$–$C_{14}$ branched chain hydrocarbons, and mixtures thereof, more preferably $C_{11}$–$C_{13}$ branched chain hydrocarbons, most preferably $C_{12}$ branched chain hydrocarbons. Saturated hydrocarbons are preferred, although it is not intended to exclude unsaturated hydrocarbons. Examples of suitable branched chain hydrocarbons include isoparaffins of the above chain sizes. Isoparaffins are commercially available from Exxon Chemical Co., USA. Examples include Isopar™ G ($C_{10}$–$C_{11}$ isoparaffins), Isopar™ H and K ($C_{11}$–$C_{12}$ isoparaffins), and Isopar™ L ($C_{11}$–$C_{13}$ isoparaffins). Most preferred are $C_{12}$ branched chain hydrocarbons, especially isododecane. Isododecane is commercially available from Preperse, Inc. (South Plainfield, N.J., USA) as Permethyl™ 99A.

Preferred siloxanes are phenyl pentamethyl disiloxane, phenylethyl pentamethyl disiloxane, hexamethyl disiloxane, methoxypropyl heptamethyl cyclotetrasiloxane, chloropropyl pentamethyl disiloxane, hydroxypropyl pentamethyl disiloxane, cyclomethicones (including octamethyl cyclotetrasiloxane and decamethyl cyclopentasiloxane), and mixtures thereof. Most preferred are cyclomethicones, more preferably octamethyl cyclotetrasiloxane and decamethyl cyclopentasiloxane.

Examples of other organic liquid diluents include benzyl alcohol, amyl acetate, propyl acetate, acetone, heptane, iso-butyl acetate, iso-propyl acetate, toluene, methyl acetate, iso-butanol, n-amyl alcohol, n-butyl alcohol, hexane, and methyl ethyl ketone.

The compositions herein more preferably comprise one, two, or three, and most preferably one or two, different organic diluents. The liquid diluents preferably consist of water, one or more liquid, volatile organic diluents suitable for topical application, or a mixture of water and one or more such organic diluents. For nail polishes according to the present invention, the most preferred organic diluents are selected from iso-propanol, n-propanol, ethanol, ethyl acetate, butyl acetate, and acetone.

In preferred lipsticks according to the present invention, the liquid diluent component is hydrophobic. The liquid diluent component of mascaras of the present invention may be hydrophobic, e.g., where water-proofness is desired, or alternatively hydrophilic or a combination thereof (e.g., emulsions and single phase mixtures). The liquid diluent component of skin care compositions, including wrinkle reducing compositions, foundations and the like, may be hydrophobic, hydrophilic, or a combination thereof (emulsions and single phase mixtures).

In preferred nail polishes according to the present invention, the liquid diluent is non-aqueous, comprises one or more hydrophilic, organic, volatile liquid diluents, and optionally one or more hydrophobic liquid diluents. The graft copolymer in such nail polishes is preferably soluble or dispersible in the hydrophilic, organic liquid diluent component, and insoluble and non-dispersible in water. The nail polish composition preferably comprises from about 10% to about 98%, more preferably from about 10% to about 90%, even more preferably from about 50% to about 90%, and most preferably from about 75% to about 90%, by weight of the composition, of one or more volatile organic liquid diluents.

The carrier can be formulated in a number of ways, including but not limited to solutions, latexes, pseudolatexes and emulsions (in emulsion technology, a composition comprising a "dispersed phase" and a "continuous phase;" the dispersed phase existing as small particles or droplets that are suspended in and surrounded by a continuous phase). For example, suitable emulsions include oil-in-water, water-in-oil, water-in-oil-in-water, oil-in-water-in-oil, and oil-in-water-in-silicone emulsions. Preferred compositions for applications to the skin, e.g., foundations, moisturizers and the like, comprise an oil-in-water emulsion.

The compositions of the present invention thus contain, in a suitable carrier, the graft copolymers described herein, for as wide a range of applications as encountered, for example, in the field of cosmetics, including skin care, make-up (e.g., color cosmetics), in which utilization of the graft copolymers is desired. The compositions of the present invention can be formulated into a wide variety of product types, including creams, lotions, milks, mousses, masks, gels, oils, tonics, serums, sprays, and lacquers. Preferred compositions are formulated into lotions, creams, gels, sprays, aerosols and lacquers. These product forms may be used for a number of applications, including, but not limited to, hand and body lotions, cold creams, facial moisturizers, anti-acne preparations, wrinkle-reducing preparations, topical analgesics, make-ups including foundations, lipsticks, mascaras, eyeliners, eyeshadows, nail polishes and the like. Any additional components required to formulate such products vary with product type and can be routinely chosen by one skilled in the art. For example, such products and their formulations to which the graft copolymers of the present invention may be added are those described in *Harry's Cosmeticology*, 7$^{th}$ Ed., R. G. Harry, J. B. Wilkinson and R. J. Moore, Chemical Pub. Co. (NY) (1982) (in particular, reference is made to pages 50–81, 119–123, 222–354, and 369–393); and *Cosmetics Science and Technology*, 2$^{nd}$ Ed., Balsam. M. S. and Sagarin, E. S., Wiley-Interscience (NY) (1972) (3 volumes) (in particular, reference is made to Vol. 1, pages 27–104, 284–305, 307–315, 317–331, 335–353, 355–363, and 365–422, and Vol. 2, pages 521–541), all incorporated herein by reference. Carriers suitable for use in the present invention are also described in U.S. Pat. No. 5,306,485 (Robinson et al.), issued Apr. 26, 1994, and U.S. Pat. No. 5,002,680 (Schmidt et al.), issued Mar. 26, 1991.

Nonlimiting examples of mascara compositions to which the present invention is applicable are also described in copending, commonly assigned U.S. patent application Ser. Nos. 08/951,285 (Alwatarri et al.), filed Oct. 16, 1997, (Attorney's Docket 6345C); Ser. No. 08/757,538 (Bartholomey et al.), filed Nov. 27, 1996 (Attorney's Docket 6397); and Ser. No. 09/121,138 (Alwatarri et al.), filed Jul. 23, 1998 (Attorney's Docket 5654C2); and in PCT Application Nos. US96/04154, published Oct. 31, 1996; US97/19786, published May 7, 1998; and US97/21890, published Jun. 4, 1998; each incorporated herein by reference in its entirety.

Nonlimiting examples of lipstick compositions to which the present invention is applicable are also described in U.S. Pat. No. 5,593,662 (Deckner et al.), issued on Jan. 14, 1997; and PCT Application Nos. US93/08684 and US 93/08683, both published Mar. 31, 1994; all incorporated herein by reference in their entirety.

Nonlimiting examples of foundation compositions to which the present invention is applicable are also described in copending, commonly assigned U.S. patent application Ser. No. 08/430,961 (Canter et al.), filed Apr. 28, 1995 (Attorney's Docket 5655); and in PCT Application No. US96/04302, published Oct. 31, 1996, incorporated herein by reference in their entirety.

If compositions of the present invention are formulated as an aerosol and applied to the skin as a spray-on product, a propellant is preferably added to the composition. Examples of suitable propellants include chlorofluorinated lower molecular weight hydrocarbons. A more complete disclosure of propellants useful herein can be found in the above-referenced *Cosmetics, Science and Technolopy*(Vol. 2, pp. 443–465).

III Optional Components

The compositions of the present invention may contain a variety of other ingredients such as are conventionally used in a given product type, provided that the advantageous properties that are intrinsic to the compositions are not, or not substantially altered by the optional component. These optional components should be suitable for topical application. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents (e.g., resorcinol, sulfur, salicylic acid, erythromycin, zinc, etc.), anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), humectants, opacifying agents, pH adjusters, propellants, reducing agents, sequestrants, skin bleaching agents (or lightening agents) (e.g., hydroquinone, kojic acid, ascorbic acid, magnesium ascorbyl phosphate, ascorbyl glucosamine), skin-conditioning agents (humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents including agents for preventing, retarding, arresting, and/or reversing skin wrinkles (e.g., alpha-hydroxy acids such as lactic acid and glycolic acid and beta-hydroxy acids such as salicylic acid), thickeners, and vitamins and derivatives thereof (e.g. tocopherol, tocopherol acetate, beta carotene, retinoic acid, retinol, retinoids, retinyl palmitate, niacin, niacinamide, and the like). The compositions of the present invention may contain one or more of such optional components.

The components herein can be categorized by the benefit they provide or by their postulated mode of action, however, it is to be understood that they can in some instances provide more than one benefit or operate via more than one mode of action. Therefore, classifications herein are made for the sake of convenience and are not intended to limit the component to the particular application or applications listed.

In particular, the nail polish compositions of the present invention may comprise a variety of optional components to enhance their performance as a nail polish. For example, antifoams, buffers, chelating agents, coalescents, dispersing agents, dyes, epoxies, fillers, pigments, preservatives, resins, therapeutic and prophylactic agents, thickeners, wax additives, wetting agents, secondary film formers, plasticizers and the like can be included in the compositions herein. Preferred nail polish compositions comprise a plasticizer and pigment. Such optional components may be dispersed, solubilized, or otherwise mixed in the carrier and/or the liquid diluent of the compositions. These components may be added to the compositions herein provided they do not substantially hinder the wear properties, particularly the adhesion, of the compositions. Non-limiting examples of such optional components are given below.

a) Pigments or Dyes

Pigments and other suitable coloring agents may be incorporated into the present compositions. Suitable pigments include inorganic or organic pigments known as, for example, the FD&C and D&C colors, lakes, and iron oxides. Such pigments are disclosed in the C.T.F.A. *Cosmetic Ingredient Handbook,* First Edition, 1988. Organic pigments include, for example, D and C Red, Nos. 10, 11, 12, and 13, D and C Red No. 7, D and C Red Nos. 5 and 6, D and C Red Nos. 30 and 34, lacquers such as D and C Yellow No. 5 and D and C Red No. 2, and guanine. Inorganic pigments include, for example, titanium dioxide, bismuth oxychloride, brown iron oxide, and the red iron oxides.

Preferably from 0% to about 5%, by weight of the composition, of a pigment or dye are used in the present nail polish compositions.

b) Plasticizers

Without intending to be limited by theory, plasticizers cause a composition to become more easily deformed. One or more plasticizers may optionally be added to the present compositions. Suitable plasticizers include those disclosed in WO 97/00664, Chen et al, assigned to Eastman Chemical Co. Suitable plasticizers include phthalates, nonionic surfactant polymers, and polyesters. Preferred plasticizers include diethyl phthalate, dibutyl phthalate, dioctyl phthalate, diethyl tartrate, dibutyl tartrate, diethyl phosphate, dibutyl phosphate, polyester sebacates, such as Paraplex G-25® (commercially available from C. P. Hall, Bedford Park, Ill.) polyester adipates, such as Paraplex G-50® (C. P. Hall) and tetraethylene glycol di-2-ethylhexoate, available as Tegmer® (C. P. Hall). The most preferred plasticizers include dibutyl phthalate, Paraplex G-25®, Paraplex G-50®, and Tegmer®.

The nail polish compositions preferably comprise from 0% to about 10%, more preferably from about 0% to about 5%, by weight of the composition, of a plasticizer.

c) Preservatives

One or more preservatives may optionally be added to the present compositions to prevent, inhibit, or retard microbial growth in the composition. Preferably, the compositions comprise a preservative wherein the composition comprises less than about 40% of one or more organic solvents. Preferred preservatives include methyl paraben, ethyl paraben, propyl paraben, benzyl alcohol, benzoic acid, benzoates (preferably sodium benzoate), sorbates (preferably potassium sorbate), sodium dehydroacetate, 1-(3-chloroallyl)-3,5,7-triaza-1-azoniaadamantane chloride (which may be obtained commercially as Quaternium-15® from Dow Chemical Co., Midland, Mich.), a mixture of 95% 1,3-dimethylol-5,5-dimethyl hydantoin and 5% 3-iodo-2-propynyl butyl carbamate (which mixture is commercially available as Glydant Plus® from Lonza, Inc., Fair Lawn, N.J.), 1,3-dimethylol-5,5-dimethyl hydantoin (commercially available as Glydant® from Lonza, Inc.), diazolidinyl urea (commercially available as Germall II® from Sutton Laboratories, Chatham, N.J.), imidazolidinyl urea (commercially available as Germall 115® from Sutton Laboratories), phenoxyethanol, and Kathon® (commercially available from Rohm and Haas Co., Philadelphia, Pa.). The most preferred preservatives include methyl paraben, ethyl paraben, propyl paraben, benzyl alcohol, benzoic acid, benzoates (preferably sodium benzoate), sorbates (preferably potassium sorbate), and sodium dehydroacetate.

The nail polish compositions preferably comprise from 0% to about 10%, more preferably from 0% to about 5%, and most preferably from 0% to about 1%, by weight of the composition, of a preservative.

d) Resins

Resins including, for example, epoxies and polyacrylics, may optionally be added. Examples of suitable resins include Polytex E75® (commercially available from Estron Chemical, Inc., Calvert City, K.Y.) and Acryloid B66® (commercially available from Rohm and Haas, Philadelphia, Pa.).

The nail polish compositions preferably comprise from 0% to about 15%, more preferably from about 0.5% to about 10%, by weight of the composition, of a resin.

e) Slip Aids

Slip aids may optionally be added to improve surface friction, water resistance, abrasion resistance, and mechanical properties. Slip aids which may be used include wax additives including, for example, animal, fossil, vegetable, mineral, or synthetic waxes. Preferred wax additives include beeswax, carob, candelilla, ozocerite, polyethylene waxes, paraffin waxes, polypropylene waxes, polytetrafluoroethylene (commercially available as Teflon® from DuPont, Wilmington, Del.), nylons, and polyamides. Specifically, preferred wax additives include, but are not limited to, Jonwax® 26 (commercially available from S.C. Johnson Polymer, Sturtevant, Wis.) Jonwax® 120 (S.C. Johnson Polymer), Chemcor 325N35, Chemcor 43N40, Glaswax® E-1 (commercially available from Allied Colloids, Suffolk, Va.), Glaswaxc® E-1235 (Allied Colloids), Drewax® EL-3030 (commercially available from Ashland Chemical, Boontown, N.J.), Drewax® E-7030 (Ashland Chemical), Lanco® PP1362D (commercially available from Lubrizol, Wichliffe, Ohio), Lanco® A1601 (Lubrizol), and Lanco® TF1780 (Lubrizol).

Other slip aids include materials containing silicone such as copolymers of polyether and polysiloxane. Examples of such slip aids include, for example, Glide 450 and Abil B-8830 (both of which are commercially available from Goldschmidt Chemical, Hopewell, Va.).

The present nail polish compositions preferably comprise from 0% to about 10%, more preferably from about 0.1% to about 10%, even more preferably from about 0.5% to about 8%, and most preferably from about 0.5% to about 3% of a slip aid.

f) Therapeutic and Prophylactic Agents

Therapeutic and/or prophylactic agents such as, for example, vitamins, proteins, anti-fungal and anti-microbial agents, and sunscreens (including UV-A, UV-B, and broad spectrum solar filters) may optionally be added to the present nail polish compositions for the further care and protection of the nails.

g) Thickeners

Thickeners may optionally be added to the present compositions to achieve desired rheology and application properties. Preferred thickeners include solution polymers (e.g., hydroxyethyl cellulose, hydroxypropyl cellulose, methyl cellulose, and other conventional cellulosic polymers), associative thickeners (e.g., hydrophobically modified cellulosic polymers, nonionic urethanes, and alkali swellable urethanes) including Aculyn® 44 (commercially available from Rohm & Haas, Philadelphia, Pa.), clays (e.g., laponite and hydrophilic montmorillonite (commercially available as Bentone® from Rheox, Hightstown, N.J.)), and natural rubbers and gums (e.g., guar gum, quaternized guar gum sold under the name Jaguar® C-13-S by Rhone-Poulenc, Shelton, Conn., hydroxypropyl guar gum, gum arabic, carob gum, carrageenan, and xanthan gum).

The present nail polish compositions preferably comprise from 0% to about 10%, more preferably from about 0.1% to about 10%, and even more preferably from about 0.1% to about 5% of a thickener, by weight of the composition.

h) Secondary Film Formers

The present nail polish compositions may contain one or more other polymeric film formers, provided that they do not substantially impair the benefits of the graft copolymer, especially through visible macrophase separation.

The film-forming polymers herein can be selected from nonionic, ionic (anionic or cationic), and amphoteric (including zwitterionic) polymers. Anionic polymers are preferred for water-borne compositions.

Suitable film-forming polymers include any such as are known in the art, such as cellulosic polymers, polyacryls, polymethacryls, styrene-acryl copolymers, polystyrenes, polysiloxanes, polyesters, urethanes, urethane-acryl copolymers, siloxane-urethane copolymers, silicone-acryl copolymers, silicone grafted polymers, silicone block copolymers, polyolefins, vinyl esters, vinyl ethers, and mixtures thereof. Preferred compositions comprise polyacryls, polymethacryls, styrene-acryl copolymers, vinyl esters and cellulosic polymers.

The film-forming cellulosic polymers may be selected from polymers derived from cellulose such as are known in the art, including but not limited to cellulose esters. Preferred cellulosic polymers are nitrocellulose, cellulose acetate, cellulose acetate butyrate, and cellulose acetate propionate. Nitrocellulose polymers are more preferred. Exemplary nitrocellulose polymers are nitrocellulose RS types (nitrogen content of 11.5–12.2%) of Hercules, such as nitrocellulose—RS ½ second, —RS ¼ second, —RS ⅛ second, —RS ¹⁄₁₆ second or the like.

As used herein, a "polyacryl" includes polyacrylates, polyacrylics, or polyacrylamides, and "polymethacryl" includes polymethacrylates, polymethacrylics, or polymethacrylamides. Styrene-acryl copolymers include copolymers of styrene with acrylate, acrylic, acrylamide, methacrylate, methacrylic, and/or methacrylamide monomers. Examples of preferred polyacryls, polymethacryls, and styrene-acryl copolymers include Gelva® 2497 (commercially available from Monsanto Co., St. Louis, Mo.), Duraplus® 2 (commercially available from Rohm & Haas Co., Philadelphia, Pa.), Joncryl® 95 (commercially available from S.C. Johnson Polymer, Sturtevant, Wis.), SCX-1537 (S.C. Johnson Polymer), SCX-1959 (S.C. Johnson Polymer), SCX-1965 (S.C. Johnson Polymer), Joncryl® 530 (S.C. Johnson Polymer), Joncryl® 537 (S.C. Johnson Polymer), Glascol LS20 (commercially available from Allied Colloids, Suffolk, Va.), Glascol C37 (Allied Colloids), Glascol LS26 (Allied Colloids), Glascol LS24 (Allied Colloids), Glascol LE45 (Allied Colloids), Surcol 441® (Allied Colloids), Carboset® C.R760 (commercially available from BFGoodrich, Cleveland, Ohio), Carboset® CR761 (BFGoodrich), Carboset® C.R763 (BFGoodrich), Carboset® 765 (BFGoodrich), Carboset® 19X2 (BFGoodrich), Carboset® 28 (BFGoodrich), Hycar 26084 (BFGoodrich), Hycar 26091 (BFGoodrich), Carbobond 26373 (BFGoodrich), Neocryl® A-601 (commercially available from Zeneca Resins, Wilmington, Mass.), Neocryl® A-612 (Zeneca Resins), Neocryl® A-6044 (Zeneca Resins), Neocryl® A-622 (Zeneca Resins), Neocryl® A-623 (Zeneca Resins), Neocryl® A-634 (Zeneca Resins), and Neocryl® A-640 (Zeneca Resins).

Preferred vinyl esters are vinyl butyrate polymers and vinyl acetate polymers.

Methods of Making and Using the Compositions

The graft copolymers can be made according to the methods disclosed herein above. The compositions of the present invention can be made using conventional formulation and mixing techniques. The compositions of the present invention include those comprising each of the essential components in addition to any optional components, as well as those prepared by a process of combining, in any order, the above described essential components as well as any optional components. The present compositions are applied to the skin, lips, eyelashes, eyelids, nails, or like topical substrate in any suitable manner such as known in the art.

For example, the nail polish compositions can be applied to nails using any suitable applicator such as are known in the art, e.g., a standard brush-applicator as is commonly utilized in the art. Sufficient liquid diluent is then removed from the applied composition (through evaporation of volatiles, most preferably at ambient pressures and temperatures), to form a substantially dry layer or film, that is, the film or layer feels dry, smooth, or not tacky when it is touched with a human fingertip.

The present nail polish compositions may be used as the sole nail polish composition, or in conjunction with other nail polishes or treatments. Other nail polish/treatment compositions may be used in conjunction with the present compositions to provide additional benefits, such as aesthetic benefits (e.g., color, shine) and/or additional performance benefits (e.g., further wear improvements). Similarly, for skin care applications, including wrinkle reducing compositions, the compositions may be applied in combination with, on top of, or underneath other cosmetic or skin care products.

The present nail polish compositions are particularly useful as topcoat compositions, in conjunction with a basecoat and optionally a midcoat composition. As used herein, a "topcoat composition" is a composition which is suitable for application to a nail to form a topcoat, which is the most distal layer of nail polish relative to layers of one or more different nail polishes which have been previously applied to the nails. The topcoat composition is more preferably applied contiguously to one (basecoat) or two (basecoat and midcoat) different, previously applied layers, most preferably two different layers.

A "basecoat composition" is a composition which is suitable for application to a nail to form a basecoat, which is the most proximal layer of nail polish relative to layers of different nail polish which are subsequently applied to the nails. The basecoat compositions comprise a film-forming polymer, a volatile liquid diluent, and, optionally, other components suitable for nail polishes such as described herein. Preferred optional components for basecoat compositions are selected from plasticizers, pigments, and dyes.

A "midcoat composition" is a composition which is suitable for application to a nail to form a midcoat, which is a layer of nail polish between a basecoat and a topcoat. The midcoat compositions comprise a film-forming polymer, a volatile liquid diluent, and, optionally, other components suitable for nail polishes such as described herein. Preferred optional components for midcoat compositions are selected from plasticizers, pigments, and dyes. The midcoat compositions preferably comprise from about 10% to about 25%, more preferably from about 10% to about 18% of a film-forming polymer, from about 60% to about 85%, more preferably from about 60% to about 80% of a volatile organic diluent (such as described herein above), and preferably 0% to about 13%, more preferably from about 5% to about 13%, and most preferably from about 6% to about 12% of a plasticizer, by weight of the composition.

Film-forming polymers comprising the midcoat compositions are preferably selected from cellulosic polymers, polyurethanes, polyacryls, polymethacryls, polysiloxanes, and mixtures thereof. More preferred film-forming polymers are polyacryls and cellulosic polymers, with cellulosic polymers being the most preferred. Preferred polyacryls for the midcoat compositions are those which are hydrophobic and/or exhibit a glass-transition temperature (Tg) of from about −10° C. to about +30° C. Wherein the polyacryl has a $T_g$ higher than about +30° C., the midcoat composition preferably comprises a plasticizer. Exemplary compositions suitable for use as midcoat compositions are commercially available such as, for example, those marketed by the Procter & Gamble Company under the Max Factor® or Cover Girl® trade names.

Suitable basecoat or midcoat compositions include those basecoats and midcoats disclosed in commonly assigned, copending U.S. patent application Ser. No. 09/070,960 (Ellingson et al.), Ser. No. 09/071,424 (Ellingson et al.), Ser. No. 09/071,098 (Ellingson et al.), Ser. No. 09/071,097 (Smith, III et al.), Ser. No. 09/071,273 (Ellingson et al.), Ser. No. 09/071,423 (Ellingson et al.), and Ser. No. 09/071,099 (Ellingson et al.), corresponding to Attorey's Docket 7140, 7141, 7142, 7143, 7144, 7145 and 7146, each filed on May 1, 1998, and each incorporated herein by reference in their entirety. Preferred basecoats and midcoats, disclosed in the aforementioned application Ser. No. 09/071,099, are as follows (in the examples herein below, all polymer component percentages are expressed in weight percent of solid polymer (based on the total composition)).

a) Preferred basecoats (BC) for use with a nail polish composition of the present invention as a topcoat:

|  | BC 1 | BC 2 | BC 3 | BC 4 | BC 5 |
|---|---|---|---|---|---|
| Duraplus 2 ® | 21% | — | — | 21% | — |
| Nitrocellulose RS ¼ second | — | 15% | — | — | 6.75% |
| Sanres ® EX499[1] | — | 3.6% | — | — | — |
| Sanres ® 12711[2] | — | 1.5% | 15.5% | — | — |
| Sanres ® 6012[3] | — | — | — | — | 8.25% |
| Surcol ® 441 | — | — | 4.5% | — | — |
| Dowanol DPnP ®[4] | 10% | — | — | 10% | — |
| Dibutyl Phthalate | 3.9% | — | — | 1.6% | — |
| Glide 450 ® | 0.3% | — | — | 0.3% | — |
| Aculyn 44 ® | 0.5% | — | — | — | — |
| Polytex E-75 (Estron Chemical) | — | 1% | — | — | — |
| Drewax E-3030 ® | — | — | — | 1.2% | — |
| Paraplex G-50 ® | — | 7.6% | — | — | — |
| Butyl Acetate | — | 32.9% | 30% | — | 40% |
| Ethyl Acetate | — | 27.4% | 10% | — | — |
| iso-Propanol | — | 11% | 30% | — | 35% |
| Toluene | — | — | — | — | 10% |
| Acetone | — | — | 10% | — | — |
| Water | 64.3% | — | — | 65.9% | — |

[1]hexylene glycol/neopentyl glycol/isophorone diisocyanate copolymer, BF Goodrich, Cleveland, OH
[2,3]solvent borne polyurethanes, BF Goodrich
[4]dipropylene glycol ether, Dow Chemical Co.

Basecoat formula BC 2 is particularly preferred.

An alternatively preferred basecoat is a conventional nail polish composition such as Max Factor® International, marketed by the Procter & Gamble Company (comprising butyl acetate, ethyl acetate, nitrocellulose, toluenesulphonamide formaldehyde resin, dibutyl phthalate, toluene, isopropanol, camphor, benzophenone, stearalkonium hectorite, and polyester resin).

b) Preferred basecoats (BC) and midcoats (MC) for use with a nail polish composition of the present invention as a topcoat:

|  | BC 6 | BC 7 | BC 8 | BC 9 |
|---|---|---|---|---|
| Sancure 2710 ®[1] | 4% | 5.5% | 5.8% | 5.8% |
| n-Propanol | 71.4% | — | 70% | — |
| Ethyl Acetate | — | 78.1% | — | — |
| iso-Propanol | | | | 32.1% |
| Ethanol | — | 7.9% | — | — |
| Water | 24.4% | 8.5% | 24% | 61.9% |

-continued

|  | BC 6 | BC 7 | BC 8 | BC 9 |
| --- | --- | --- | --- | --- |
| Methyl Paraben | 0.1% | — | 0.1% | 0.1% |
| Propyl Paraben | 0.1% | — | 0.1% | 0.1% |

[1]copolymer of polypropylene glycol, isophorone diisocyanate, and 2,2-dimethylolpropionic acid, having the International Nomenclature Cosmetic Ingredient name "PPG-17/PPG-34/IPDI/DMPA Copolymer", BF Goodrich, Cleveland, OH Preferred midcoats for use with the above basecoat formulas BC 6–BC 9 are as described above. Particularly preferred is a conventional polish such as the above-described Max Factor® International.

The present invention includes a method of coating nails with a nail polish film, wherein the film comprises one or more layers of different nail polishes. In one embodiment, the method comprises the steps of:

(i) applying to nails a nail polish composition of the present invention; and (ii) substantially drying the composition applied to the nail to form a nail polish film.

Another embodiment of the present invention is a method comprising the steps of:

(i) applying a basecoat composition contiguously to the nail, wherein the basecoat composition comprises a film-forming polymer and a carrier suitable for application to nails comprising a volatile liquid diluent;

(ii) substantially drying the basecoat composition applied to the nail to form a basecoat layer;

(iii) then optionally applying a midcoat composition to the nail, wherein the midcoat composition comprises a film-forming polymer and a volatile liquid diluent;

(iv) substantially drying the midcoat composition applied to the nail to form a midcoat layer;

(v) then applying a nail polish composition of the present invention, preferably as a topcoat composition, to the nail; and (vi) substantially drying the composition of the present invention applied to the nail to form a nail polish layer, preferably a topcoat layer.

EXAMPLES

Each of the examples herein further describe and demonstrate embodiments within the scope of the present invention. The examples are given solely for the purpose of illustration and are not to be construed as limitations of the present invention, as many variations thereof are possible without departing from the spirit and scope of the invention.

EXAMPLES OF GRAFT COPOLYMER SYNTHESIS

Polymer Synthesis Example 1 p-Vinyl benzoyl chloride: p-vinyl benzoic acid (10 g, 0.067 mole) is suspended in benzene (25 ml). Oxalyl chloride (25 g, 0.2 mole) is added. The mixture is stirred for 8 hours under argon atmosphere. Solvent and excess oxalyl chloride is removed in vacuo. The product is distilled in vactio to yield p-vinyl benzoyl chloride.

Vinylphenyl-terminated Poly(n-propyl methacrylate-co-methacrylic acid) macromonomer: In a flask under slight argon pressure (8 psi) is added tetrahydrofuran (THF) (1 L), trimethylsilylmethacrylate (100 g, 0.63 mole), and n-propylmethacrylate (100 g, 0.78 mole). The solution is cooled to −80° C. and initiated with diphenylhexyllithium (0.0275 mole) (prepared by adding 1:1 mole ratio of sec-butyl lithium and 1,1-diphenyl ethylene in THF) for chain propagation via anionic polymerization mechanism. After continuous stirring for 30 minutes, vinylbenzoyl chloride (8.33 mL, 0.05 mole) is charged to the solution and stirring is continued for 30 minutes. The solution is warmed to ambient temperature and water (10 mL) is added and stirred for approximately 15 minutes hours to deprotect the acid groups. The macromonomer ($M_w$ 6000), is obtained by precipitating the resulting solution in hexanes, collecting the precipitate, and drying in vacuo.

Polymer Synthesis Example 2

Poly (t-butylacrylate-co-2-methoxyethylacrylate-co-acrylic acid)-graft -[poly(n-propyl methacrylate-co-methacrylic acid)poly(dimethylsiloxane)] copolymer: To a flask equipped with a reflux condenser, temperature control, mechanical stirring mechanism, and slight argon pressure (8 psi), is added acetone (0.5 L), 1-butylacrylate (22.3 g), 2-methoxyethylacrylate (36 g), acrylic acid (18 g), poly (dimethylsiloxane) macromonomer (6 g) (obtainable from Chisso Corp. Tokyo, Japan), and vinylphenyl-terminated (n-propylmethacrylate-co-methacrylic acid) macromonomer (18 g). The solution is stirred until all components are dissolved, then heated to 60° C. Azobisisobutyronitrile (0.7 g) is charged to the solution. After 10 hours, the solution is cooled and precipitated in water to yield the desired silicone modified graft copolymer.

Polymer Synthesis Example 3

Poly(t-butylacrylate-co-2-methoxyethylacrylate-co-methacrylic acid)-graft-[poly(n-propyl methacrylate-co-methacrylic acid) copolymer: To a flask equipped with a reflux condenser, temperature control, mechanical stirring mechanism, and slight argon pressure (8 psi), is added acetone (0.5 L), t-butylacrylate (42.4 g), 2-methoxyethyl acrylate (29 g), methacrylic acid (9 g), and vinylphenyl-terminated (n-propylmethacrylate-co-methacrylic acid) macromonomer (20 g). The solution is stirred until all components are dissolved, then heated to 60° C. Azobisisobutyronitrile (0.5 g) is charged to the solution. After 10 hours, the solution is cooled and precipitated in water to yield the desired graft copolymer.

Polymer Synthesis Example 4

Poly(2-methoxyethyl acrylate-co-methacrylic acid-co-t-butyl acrylate-)-graft-poly(styrene-co-methacrylic acid).

Into an argon purged round-bottomed-flask equipped with mechanical stirring and a reflux condenser, is added butyl acetate (1 L), trimethylsilylmethacrylate (18.4 g, 0.116 mole), t-butylacrylate (27.2 g, 0.212 mole), 2-methoxyethyl acrylate (31.4 g, 0.241 mole), and chloromethyl styrene (0.4 g, 0.003 mole). The solution is heated to 60° C. then initiated with AIBN (azobisisobutyronitrile) (0 g, 0.006 mole) and allowed to undergo free radical polymerization for 10 hours. The resulting solution is then heated to 100° C. and allowed to cool. When the solution reaches ambient temperature, trimethylsilylmethacrylate (22.0 g, 0.139 mole), styrene (18.0 g, 0.173 mole), 2,2'-dipyridyl (1.4 g, 0.009 mole), and Cu(I)Cl (0.3 g, 0.003 mole) are added. The solution is then heated to 120° C. with stirring for 6 hours. The solution is then cooled to ambient temperature and catalyst is removed via vacuum filtration. The filtrate is diluted with acetone (200 ml) and water (10 ml) and stirred for 2 hours.

The resulting solution is precipitated into hexanes and the graft polymer collected and dried.

Polymer Synthesis Example 5

Poly(2-methoxyethyl acrylate-co-methacrylic acid-co-t-butyl)-graft-[poly(styrene-co-methacrylic acid); poly(dimethylsiloxane)].

Into an argon purged round-bottomed-flask equipped with mechanical stirring and a reflux condenser, is added butyl acetate (1 L), trimethylsilyl methacrylate (18.4 g, 0.116 mole), t-butylacrylate (27.2 g, 0.212 mole), 2-methoxyethyl acrylate (26.4 g, 0.203 mole), polydimethylsiloxane macromonomer (molecular weight 10,000)(available from Chisso Corp., Tokyo, Japan) (5 g), and chloromethyl styrene (0.4 g, 0.003 mole). The solution is heated to 60° C. then initiated with AIBN (1.0 g, 0.006 mole) and allowed to undergo free radical polymerization for 10 hours. The resulting solution is then heated to 100° C. then allowed to cool. When solution reaches ambient temperature, trimethylsilyl-methacrylate (22.0 g, 0.139 mole), styrene (18.0 g, 0.173 mole), 2,2'-dipyridyl (1.4 g, 0.009 mole), and Cu(I)Cl (0.3 g, 0.003 mole) are added. The solution is heated to 120° C. with stirring for 6 h. The solution is then cooled to ambient temperature and catalyst is removed via vacuum filtration. Filtrate is diluted with acetone (200 ml) and water (10 ml) and stirred for 2 hours. The resulting solution is precipitated into hexanes and the graft polymer collected and dried.

EXAMPLES OF COSMETIC COMPOSITIONS

In the examples herein below, all component percentages are based on weight of the total composition. The polymer component percentages are expressed in weight percent of solid polymer (based on the total composition).

Examples 6–8

The compositions of Examples 6–8 are representative nail polishes of the present invention:

|  | Ex. 6 | Ex. 7 | Ex. 8 |
| --- | --- | --- | --- |
| Copolymer 1* | — | — | 10.4% |
| Copolymer 4** | 20% | 20% | — |
| Ethanol | 35% | 65% | 34% |
| n-Butanol | 45% | 15% | — |
| iso-Propanol | — | — | 55% |
| Polytex E75 ® | — | — | 0.6% |

*Poly(t-butyl acrylate-co-2-methoxyethyl acrylate-co-methacrylic acid)-graft-poly (n-propyl methacrylate-co-methacrylic acid)
**Poly(t-butyl acrylate-co-2-methoxyethyl acrylate-co-acrylic acid)-graft-[poly (n-propyl methacrylate-co-methacrylic acid) poly(dimethylsiloxane)]

This product is prepared by mixing all the ingredients until dispersed.

Example 9

The following is a nail polish clear coat composition representative of the present invention.

| Copolymer from synthesis example 3* | 15.00 |
| --- | --- |
| Ethanol | 42.00 |
| Acetone | 40.00 |
| NaOH soln., 30% | 3.00 |

*Poly(t-butylacrylate-co-2-methoxyethylacrylate-co-methacrylic acid)-graft-[poly(n-propyl methacrylate-co-methacrylic acid) copolymer

Example 10

The following is an eyeliner representative of the present invention.

| Copolymer 6* | 10.00 |
| --- | --- |
| Black Iron Oxide | 10.00 |
| Triethanolamine | 4.00 |
| Deionized Water | q.s. |

*Poly((t-butyl acrylate-co-2-methoxyethyl acrylate-co-methacrylic acid)-graft-poly(2-ethyl 2-oxazoline))

Example 11

The following is a mascara according to the present invention.

| Copolymer 4* | 10.00 |
| --- | --- |
| Carnauba Wax | 3.50 |
| Glycerol Monostearate | 7.00 |
| Quaternium-18 Hectorite[1] | 3.75 |
| Propylene Carbonate | 1.25 |
| Stearic Acid | 2.75 |
| Oleic Acid | 1.00 |
| Triethanolamine | 3.50 |
| Trisodium EDTA | 0.10 |
| Propylene Glycol | 2.00 |
| Simethicone[2] | 0.20 |
| Ammonium Acrylates Copolymer[3] | 12.00 |
| Lecithin | 1.25 |
| Benzyl Alcohol | 0.65 |
| Phenoxyethanol | 0.28 |
| Propylparaben | 0.10 |
| Methylparaben | 0.20 |
| Ethylparaben | 0.20 |
| Deionized Water | q.s. |

*Poly(t-butyl acrylate-co-2-methoxyethyl acrylate-co-acrylic acid)-graft-[poly (n-propyl methacrylate-co-methacrylic acid) poly(dimethylsiloxane)]
[1]available as Bentone 38 from Rheox
[2]available as Antifoam from Dow Corning
[3]available as Syntran EX33-1 (41% Stock Solution) from Interpolymer Corporation.

Example 12

The following is a facial wrinkle remover composition representative of the present invention.

| Copolymer 2* | 6.00 |
| --- | --- |
| NaOH soln., 30% | 2.10 |
| DRO water | q.s. |

*Poly(t-butyl acrylate-co-2-methoxyethyl acrylate-co-methacrylic acid)-graft-poly(iso-butyl methacrylate-co-methacrylic acid)

Example 13

The following is a lipstick composition representative of the present invention.

| | |
|---|---|
| Copolymer 7* | 10.00 |
| Red 17 Calcium Lake | 3.00 |
| Yellow 5 Aluminum Lake | 3.00 |
| Carnauba Wax | 5.00 |
| Hydrogenated Vegetable Oil | 8.00 |
| Acetylated Lanolin | 7.00 |
| Bismuth oxychloride | 5.00 |
| Isododecane[1] | q.s. |

*Poly((iso-butyl methacrylate-co-2-ethylhexyl methacrylate)-graft-poly(2-ethyl 2-oxazoline))
[1] available as Permethyl 99A

What is claimed is:

1. A method of coating nails with a nail polish film comprising the steps of:
   (i) applying a nail polish composition to the nail, wherein the nail polish composition comprises:
      (a) from about 1% to about 40%, based on the weight of the composition, of a film-forming graft copolymer, wherein the copolymer comprises:
         (I) a backbone exhibiting a $T_g$ of from about 0° C. to about 50° C., and
         (II) one or more hydrophilic grafts attached to the backbone wherein each of the grafts exhibits a $T_g$ of from about 50° C. to about 200° C., and wherein the average molecular weight of each of the grafts is greater than about 1000; and
      (b) from about 60% to about 99%, based on the weight of the composition, of a carrier suitable for application to the nails, wherein the carrier comprises from about 10% to about 98%, based on the weight of the composition, of a volatile liquid organic diluent; and
   (ii) substantially drying the composition applied to the nail to form a nail polish film.

2. The method of claim 1 wherein the composition is applied contiguously to the nail.

3. A method of coating nails with a nail polish film comprising the steps of:
   (i) applying a basecoat composition contiguously to the nail, wherein the basecoat composition comprises a film-forming polymer and a liquid diluent;
   (ii) substantially drying the basecoat composition applied to the nail to form a basecoat layer;
   (iii) then optionally applying a midcoat composition to the nail, wherein the midcoat composition comprises a film-forming polymer and a liquid diluent; and
   (iv) substantially drying the midcoat composition applied to the nail to form a midcoat layer;
   (v) then applying a topcoat composition to the nail, wherein the topcoat composition comprises:
      (a) from about 1% to about 40%, based on the weight of the composition, of a film-forming graft copolymer, wherein the copolymer comprises:
         (I) a backbone exhibiting a $T_g$ of from about 0° C. to about 50° C.; and
         (II) one or more hydrophilic grafts attached to the backbone wherein each of the grafts exhibits a $T_g$ of from about 50° C. to about 200° C., and wherein the average molecular weight of each of the grafts is greater than about 1000; and
      (b) from about 60% to about 99%, based on the weight of the composition, of a carrier suitable for application to the nails, wherein the carrier comprises from about 10% to about 98%, based on the weight of the composition, of a volatile liquid organic diluent; and
   (vi) substantially drying the topcoat composition applied to the nail to form a topcoat layer.

* * * * *

UNITED STATES PATENT AND TRADEMARK OFFICE
CERTIFICATE OF CORRECTION

PATENT NO. : 6,106,820
DATED : August 22, 2000
INVENTOR(S) : C.T. Morrissey et al.

It is certified that error appears in the above-identified patent and that said Letters Patent is hereby corrected as shown below:

Column 3,
Line 66, "arc" should read -- are --.

Column 7,
Line 32, "$C_1$-$C_6$ alkylamino" should read -- $C_2$-$C_6$ alkylamino --
Line 50, the structure " 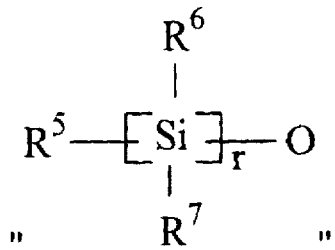 "

should read

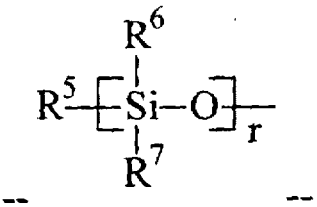

Column 8,
Line 29, "250.000" should read -- 250,000 --.
Line 42, "(1 8%)" should read -- (18%) --.

Column 9,
Line 3, "anionic." should read -- anionic, --.

Column 18,
Line 42, "C.R763" should read -- CR763 --.
Line 44, "Carboset® 28" should read -- Carboset® XL28 --

UNITED STATES PATENT AND TRADEMARK OFFICE
CERTIFICATE OF CORRECTION

PATENT NO. : 6,106,820
DATED : August 22, 2000
INVENTOR(S) : C.T. Morrissey et al.

It is certified that error appears in the above-identified patent and that said Letters Patent is hereby corrected as shown below:

Column 20,
Line 10, "Attorey's" should read -- Attorney's --.

Column 21,
Line 63, "vactio" should read -- vacuo --.

Column 22,
Line 21, "1-butylacrylate" should read -- t-butylacrylate --.

Signed and Sealed this

Fifth Day of March, 2002

*Attest:*

JAMES E. ROGAN
*Director of the United States Patent and Trademark Office*

*Attesting Officer*